United States Patent
Li et al.

(10) Patent No.: US 11,512,141 B2
(45) Date of Patent: Nov. 29, 2022

(54) FIBRINOGEN-LIKE PROTEIN 2 (FGL2) MONOCLONAL ANTIBODIES AND THEIR USE IN CANCER DETECTION AND TREATMENT

(71) Applicant: Board of Regents, The University of Texas System, Austin, TX (US)

(72) Inventors: Shulin Li, Houston, TX (US); Jun Yan, Houston, TX (US); Jiemiao Hu, Houston, TX (US); Xueqing Xia, Houston, TX (US); Qingnan Zhao, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 76 days.

(21) Appl. No.: 16/610,825

(22) PCT Filed: May 7, 2018

(86) PCT No.: PCT/US2018/031432
§ 371 (c)(1),
(2) Date: Nov. 4, 2019

(87) PCT Pub. No.: WO2018/204928
PCT Pub. Date: Nov. 8, 2018

(65) Prior Publication Data
US 2020/0055955 A1    Feb. 20, 2020

Related U.S. Application Data

(60) Provisional application No. 62/501,870, filed on May 5, 2017.

(51) Int. Cl.
| | | |
|---|---|---|
| *C07K 16/36* | (2006.01) | |
| *A61P 35/00* | (2006.01) | |
| *A61K 31/437* | (2006.01) | |
| *A61K 31/505* | (2006.01) | |
| *A61K 31/706* | (2006.01) | |
| *A61K 39/395* | (2006.01) | |
| *G01N 33/574* | (2006.01) | |
| *A61K 39/00* | (2006.01) | |
| *C07K 16/28* | (2006.01) | |

(52) U.S. Cl.
CPC ............ *C07K 16/36* (2013.01); *A61K 31/437* (2013.01); *A61K 31/505* (2013.01); *A61K 31/706* (2013.01); *A61K 39/3955* (2013.01); *A61P 35/00* (2018.01); *C07K 16/2818* (2013.01); *G01N 33/57492* (2013.01); *A61K 2039/505* (2013.01); *C07K 2317/76* (2013.01); *G01N 2333/75* (2013.01)

(58) Field of Classification Search
CPC ................ C07K 16/2818; C07K 16/36; C07K 2317/76; A61P 35/00; A61K 31/437; A61K 31/495; A61K 31/505; A61K 31/706; A61K 39/3955; A61K 2039/505; A61K 2039/507; G01N 33/57492; G01N 2333/75
See application file for complete search history.

(56) References Cited

U.S. PATENT DOCUMENTS

| | | |
|---|---|---|
| 8,076,300 B2 | 12/2011 | Presta et al. |
| 2003/0103976 A1 | 6/2003 | Serizawa et al. |
| 2005/0169913 A1 | 8/2005 | Levy et al. |
| 2007/0128198 A1 | 6/2007 | Levy et al. |
| 2016/0235841 A1 | 8/2016 | Bush |

FOREIGN PATENT DOCUMENTS

| | | |
|---|---|---|
| CN | 1958801 | 5/2007 |
| CN | 102085378 | 6/2011 |
| CN | 102358751 | 2/2012 |
| WO | WO 2017-066561 | 4/2017 |
| WO | WO 2018/204928 | 11/2018 |
| WO | WO 2020/097236 | 5/2020 |

OTHER PUBLICATIONS

Latha et al., "The Role of Fibrinogen-Like Protein 2 on Immunosuppression and Malignant Progression in Glioma," *J Natl Cancer Inst.*, 111(3):292-300, 2019.
Li et al., "Novel antibody against a glutamic acid-rich human fibrinogen-like protein 2-derived peptide near Ser91 inhibits hfgl2 prothrombinase activity," *PLoS ONE*, 9(4):1-13, 2014.
PCT International Search Report and Written Opinion issued in International Application No. PCT/US2018/031432, dated Jul. 27, 2018.
PCT International Search Report and Written Opinion issued in International Application No. PCT/US2019/060120, dated Mar. 17, 2020.
Shalev et al., "The Role of FGL2 in the Pathogenesis and Treatment of Hepatitis C Virus Infection," *Rambam Maimonides Med J.*, 1(1):e0004, 2010.
Tanaka et al., "Establishment of neutralizing rat monoclonal antibodies for fibroblast growth factor-2," *Monoclonal Antibodies in Immunodiagnosis and Immunotherapy*, 33(4):261-269, 2014.
UniProtKB Accession No. A0A316VDC9 "Uncharacterized protein," 2018.
Yan et al., "FGL2 as a multimodality regulator of tumor-mediated immune suppression and therapeutic target in gliomas," *J Natl Cancer Inst*, 107(8):1-10, 2015.
Yan et al., "FGL2 promotes tumor progression in the CNS by suppressing CD103(+) dendritic cell differentiation," *Nat Commun.*, 10(1):448, 2019.
Nduom et al., "Immunosuppressive mechanisms in glioblastoma," *Neuro Oncol.*, 17(Suppl 7):vii9-vii14, 2015.
Office Action issued in Chinese Application No. 2018800418860, dated Jul. 20, 2022, and English translation thereof.

*Primary Examiner* — Robert S Landsman
(74) *Attorney, Agent, or Firm* — Parker Highlander PLLC

(57) ABSTRACT

Provided herein are anti-FGL2 monoclonal antibodies. Further provided herein are methods to reverse suppressive immune mechanisms, such as for the treatment of cancer or infectious diseases.

20 Claims, 16 Drawing Sheets

Specification includes a Sequence Listing.

| | ROI | |
|---|---|---|
| | DBT-Ctrl | DBT-FGL2KD |
| Day 1 | 3.44E+07 | 3.90E+07 |
| Day 7 | 9.52E+09 | 5.15E+06 |

SEQUENCE LISTING

<160> NUMBER OF SEQ ID NOS: 10

<210> SEQ ID NO 1
<211> LENGTH: 417
<212> TYPE: DNA
<213> ORGANISM: Artificial sequence
<220> FEATURE:
<223> OTHER INFORMATION: Synthetic oligonucleotide

<400> SEQUENCE: 1

```
atgggatgga gctgtatcat cctcttcttg gtagcaacag ctacaggtgt ccactctcag    60
gtccaactgc agcagcctgg ggctgagctt gtgaagcctg ggcttcagt gaagctgtcc    120
tgcaaggctt ctggctacac cttcgccagc tactggatgc agtgggtaaa acagaggcct   180
ggacagggcc ttgagtggat cggagagatt gatccttctg atagctatac taactacaat   240
caaaagttca aggcaaggc cacattgact gtagacacat cctccaacac agcctacatg    300
cagctcagca gcctgacatc tgaggactct gcggtctatt actgtgcaag aaatgggaat   360
tactacggta gtacctacga ctactggggc caaggcacca ctctcacagt ctcctca      417
```

<210> SEQ ID NO 2
<211> LENGTH: 139
<212> TYPE: PRT
<213> ORGANISM: Artificial sequence
<220> FEATURE:
<223> OTHER INFORMATION: Synthetic polypeptide

<400> SEQUENCE: 2

```
Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Ala Ser Tyr Trp Met Gln Trp Val Lys Gln Arg Pro Gly Gln Gly Leu
    50                  55                  60

Glu Trp Ile Gly Glu Ile Asp Pro Ser Asp Ser Tyr Thr Asn Tyr Asn
65                  70                  75                  80

Gln Lys Phe Lys Gly Lys Ala Thr Leu Thr Val Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Asn Gly Asn Tyr Tyr Gly Ser Thr Tyr Asp Tyr
        115                 120                 125

Trp Gly Gln Gly Thr Thr Leu Thr Val Ser Ser
    130                 135
```

<210> SEQ ID NO 3
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 3

```
atgatgtcct ctgctcagtt ccttggtctc ctgttgctct gttttcaagg taccagatgt    60
gatatccaga tgacacagac tacatcctcc ctgtctgcct ctctgggaga cagagtcacc   120
atcagttgca gggcaagtca ggacgttagc aattatttaa actggtatca gcagaaacca   180
gatggatctg ttaaactcct gatctactac acttcaagat acactcagg agtcccatca    240
aggttcagtg gcagtgggtc tggagcacat tattctctca ccattagcaa cctggagcaa   300
gaagatattg ccacttactt ttgccaacag ggtaatacgc ttcctccgtg acgttcggt    360
ggaggcacca agctggaaat caag                                          384
```

```
<210> SEQ ID NO 4
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 4

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Val Ser Asn Tyr Leu Asn Trp Tyr Gln Gln Lys Pro Asp Gly Ser Val
        50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Ala His Tyr Ser Leu Thr Ile Ser
                85                  90                  95

Asn Leu Glu Gln Glu Asp Ile Ala Thr Tyr Phe Cys Gln Gln Gly Asn
                100                 105                 110

Thr Leu Pro Pro Trp Thr Phe Gly Gly Gly Thr Lys Leu Glu Ile Lys
            115                 120                 125

<210> SEQ ID NO 5
<211> LENGTH: 5
<212> TYPE: PRT
<213> ORGANISM: Artificial sequence
<220> FEATURE:
<223> OTHER INFORMATION: Synthetic peptide

<400> SEQUENCE: 5

Ser Tyr Trp Met Gln
1               5

<210> SEQ ID NO 6
<211> LENGTH: 17
<212> TYPE: PRT
<213> ORGANISM: Artificial sequence
<220> FEATURE:
<223> OTHER INFORMATION: Synthetic peptide

<400> SEQUENCE: 6

Glu Ile Asp Pro Ser Asp Ser Tyr Thr Asn Tyr Asn Gln Lys Phe Lys
1               5                   10                  15

Gly

<210> SEQ ID NO 7
<211> LENGTH: 11
<212> TYPE: PRT
<213> ORGANISM: Artificial sequence
<220> FEATURE:
<223> OTHER INFORMATION: Synthetic peptide

<400> SEQUENCE: 7

Asn Gly Asn Tyr Tyr Gly Ser Thr Tyr Asp Tyr
1               5                   10

<210> SEQ ID NO 8
<211> LENGTH: 11
```

```
<212> TYPE: PRT
<213> ORGANISM: Artificial sequence
<220> FEATURE:
<223> OTHER INFORMATION: Synthetic peptide

<400> SEQUENCE: 8

Arg Ala Ser Gln Asp Val Ser Asn Tyr Leu Asn
1               5                   10

<210> SEQ ID NO 9
<211> LENGTH: 7
<212> TYPE: PRT
<213> ORGANISM: Artificial sequence
<220> FEATURE:
<223> OTHER INFORMATION: Synthetic peptide

<400> SEQUENCE: 9

Tyr Thr Ser Arg Leu His Ser
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic peptide

<400> SEQUENCE: 10

Gln Gln Gly Asn Thr Leu Pro Pro Trp Thr
1               5                   10
```

FIBRINOGEN-LIKE PROTEIN 2 (FGL2) MONOCLONAL ANTIBODIES AND THEIR USE IN CANCER DETECTION AND TREATMENT

The present application is a national phase application under 35 U.S.C. § 371 of International Application No. PCT/US2018/031432, filed May 7, 2018, which claims the priority benefit of U.S. Provisional Application Ser. No. 62/501,870, filed May 5, 2017, the entire contents of each of which are hereby incorporated by reference.

INCORPORATION OF SEQUENCE LISTING

The sequence listing that is contained in the file named "UTFCP1322WO_ST25.txt", which is 6 KB (as measured in Microsoft Windows®) and was created on May 7, 2018, is filed herewith by electronic submission and is incorporated by reference herein.

BACKGROUND

1. Field

The present invention relates generally to the fields medicine and immunology. More particularly, it concerns monoclonal antibodies against FGL2 and methods of their use, such as in treating cancer.

2. Description of Related Art

While monoclonal antibodies targeting immune checkpoints (e.g., PD-L1, PD-1, and CTLA-4) have shown promise in the treatment of some cancers, cancers such as glioblastoma multiforme (GBM) have multiple, redundant immune-suppressive mechanisms which reduce the efficacy of immunotherapy.

Fibrinogen-like protein 2 (FGL2) is a protein that exhibits pleiotropic effects within the body and is an important immune regulator of both innate and adaptive responses. FGL2 possesses prothrombinase activity and immune regulatory functions in viral infection, allograft rejection, and abortion (Selzner et al., 2010). Some investigators have suggested that FGL2 acts as a regulatory T cell effector molecule by suppressing T cell activities in a FoxP3-dependent manner Others have found that FGL2 suppresses dendritic cell (DC) and B cell functions by binding to FcγRIIB. Furthermore, emerging data demonstrates that FGL2 regulates adaptive immunity via Th1 and Th2 cytokines. Recent studies have also shown that FGL2 can promote hepatocellular carcinoma xenograft tumor growth and angiogenesis, suggesting a tumor-promoting function.

It has been shown that FGL2 may promote GBM cancer development by inducing multiple immune-suppression mechanisms (Yan et al., 2015). The data in the Yan et al. study showed that FGL2 can function as a promoter of GBM progression by upregulating negative immune checkpoint expression and may be a therapeutic target. Thus, therapies blocking FGL2 may have a broad impact for reversing immune suppression system and may work in tumors that may not respond to other treatments. Accordingly, there is a need for monoclonal antibodies targeting FGL2 for the treatment of cancer.

SUMMARY

In certain embodiments, the present disclosure provides anti-FGL2 antibodies and methods of their use. In a first embodiment, there is provided an isolated monoclonal antibody, wherein the antibody specifically binds FGL2 and comprises CDRs 1-3 of the $V_H$ domain and CDRs 1-3 of the $V_L$ domain of the antibody encoded by hybridoma clone F48 or F59. In some aspects, the antibody comprises (a) a first $V_H$ CDR at least 80% identical to $V_H$ CDR1 of F48 (SEQ ID NO: 5) or F59; (b) a second $V_H$ CDR at least 80% identical to $V_H$ CDR2 of F48 (SEQ ID NO: 6) or F59; (c) a third $V_H$ CDR at least 80% identical to $V_H$ CDR3 of F48 (SEQ ID NO: 7) or F59; (d) a first $V_L$ CDR at least 80% identical to $V_L$ CDR1 of F48 (SEQ ID NO: 8) or F59; (e) a second $V_L$ CDR at least 80% identical to $V_L$ CDR2 of F48 (SEQ ID NO: 9) or F59; and (f) a third $V_L$ CDR at least 80% identical to $V_L$ CDR3 of F48 (SEQ ID NO: 10) or F59.

In certain aspects, the antibody comprises a first $V_H$ CDR at least 90% identical to SEQ ID NO: 5, a second $V_H$ CDR at least 90% identical to SEQ ID NO: 6, a third $V_H$ CDR at least 90% identical to SEQ ID NO: 7, a first $V_L$ CDR at least 90% identical to SEQ ID NO: 8, a second $V_L$ CDR at least 90% identical to SEQ ID NO: 9, and a third $V_L$ CDR at least 90% identical to SEQ ID NO: 10. In a specific aspect, the antibody comprises a first $V_H$ CDR is identical to SEQ ID NO: 5, a second $V_H$ CDR is identical to SEQ ID NO: 6, a third $V_H$ CDR is identical to SEQ ID NO: 7, a first $V_L$ CDR is identical to SEQ ID NO: 8, a second $V_L$ CDR is identical to SEQ ID NO: 9, and a third $V_L$ CDR is identical to SEQ ID NO: 10.

In some aspects, the antibody comprises CDRs 1-3 of the $V_H$ domain and CDRs 1-3 of the $V_L$ domain of the antibody encoded by hybridoma clone F48 (SEQ ID NOs:1-4). In certain aspects, the antibody comprises CDRs 1-3 of the $V_H$ domain and CDRs 1-3 of the $V_L$ domain of the antibody encoded by hybridoma clone F59. A skilled artisan would immediately recognize the sequences corresponding the $V_H$ and $V_L$ domain CDR sequences, as the positioning of these sequences is well known in the art (see, e.g., Kabat et al., 1987, which is incorporated herein by reference).

In certain aspects, the antibody comprises a $V_H$ domain at least about 80% (e.g., 85%, 86%, 87%, 88%, 89%, 90%, 91%, 92%, 93%, 94%, 95%, 96%, 97%, 98%, 99%, or 100%) identical to the $V_H$ domain of F48 (SEQ ID NOs:1-2) and a $V_L$ domain at least about 80% (e.g., 85%, 86%, 87%, 88%, 89%, 90%, 91%, 92%, 93%, 94%, 95%, 96%, 97%, 98%, 99%, or 100%) identical to the $V_L$ domain of F48 (SEQ ID NOs:3-4). In some aspects, the antibody comprises a $V_H$ domain identical to the $V_H$ domain of F48 (SEQ ID NOs: 1-2) and a $V_L$ domain identical to the $V_L$ domain of F48 (SEQ ID NOs:3-4).

In some aspects, the antibody comprises a $V_H$ domain at least about 80% (e.g., 85%, 86%, 87%, 88%, 89%, 90%, 91%, 92%, 93%, 94%, 95%, 96%, 97%, 98%, 99%, or 100%) identical to the $V_H$ domain of F59 and a $V_L$ domain at least about 80% (e.g., 85%, 86%, 87%, 88%, 89%, 90%, 91%, 92%, 93%, 94%, 95%, 96%, 97%, 98%, 99%, or 100%) identical to the $V_L$ domain of F59. In some aspects, the antibody comprises a $V_H$ domain identical to the $V_H$ domain of F59 and a $V_L$ domain identical to the $V_L$ domain F59. In one specific aspect, the antibody is the F48 or F59 antibody. In further aspects, the antibody is recombinant.

In additional aspects, the antibody is an IgG, IgM, IgA or an antigen binding fragment thereof. In certain aspects, the antibody is a Fab', a F(ab')2, a F(ab')3, a monovalent scFv, a bivalent scFv, or a single domain antibody. In specific aspects, the antibody may be a human, humanized antibody or de-immunized antibody. In some aspects, the antibody is conjugated to an imaging agent, a chemotherapeutic agent, a toxin or a radionuclide.

A further embodiment of the present disclosure provides a composition comprising an antibody of the embodiments and aspects described herein in a pharmaceutically acceptable carrier.

In still a further embodiment, the present disclosure provides an isolated polynucleotide molecule comprising a nucleic acid sequence encoding an antibody of the embodiments and aspects described herein.

Yet still a further embodiment provides a recombinant polypeptide comprising an antibody $V_H$ domain comprising CDRs 1-3 of the $V_H$ domain of F48; or CDRs 1-3 of the $V_H$ domain of F59.

In still a further embodiment, there is provided a recombinant polypeptide comprising an antibody $V_L$ domain comprising CDRs 1-3 of the $V_L$ domain of F48 or F59.

Another further embodiment provides an isolated polynucleotide molecule comprising a nucleic acid sequence encoding a polypeptide of the embodiments and aspects described herein.

In still yet a further embodiment, the present disclosure provides a host cell comprising one or more polynucleotide molecule(s) encoding an antibody of the embodiments and aspects described herein or a recombinant polypeptide of the embodiments and aspects described herein. In some aspects, the host cell is a mammalian cell, a yeast cell, a bacterial cell, a ciliate cell or an insect cell.

Yet a further embodiment of the present disclosure provides a method of manufacturing an antibody comprising (a) expressing one or more polynucleotide molecule(s) encoding a $V_L$ and $V_H$ chain of an antibody of the embodiments and aspects described herein in a cell; and (b) purifying the antibody from the cell.

A further embodiment provides a composition comprising an effective amount of an antibody of any the embodiments and aspects described herein for the treatment of cancer in a subject. Also provided herein is the use of a composition comprising an effective amount of an antibody of the embodiments and aspects described herein for the treatment of cancer in a subject.

In a further embodiment, the present disclosure provides a method for treating a subject having a cancer comprising administering an effective amount of an antibody of any one of the embodiments and aspects described herein. In certain aspects, the cancer is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In particular aspects, the cancer is glioblastoma, lung cancer, or melanoma. In particular aspects, the antibody is in a pharmaceutically acceptable composition. In some specific aspects, the antibody is administered systemically. In other aspects, the antibody is administered intravenously, intradermally, intratumorally, intramuscularly, intraperitoneally, subcutaneously, or locally.

In further aspects, the method additionally comprises administering at least a second anticancer therapy to the subject. In some of these aspects, the second anticancer therapy is a surgical therapy, chemotherapy, radiation therapy, cryotherapy, hormonal therapy, immunotherapy or cytokine therapy. In particular aspects, the second anticancer therapy is chemotherapy. In some aspects, the chemotherapy is temolozomide or azacitidine. In further aspects, the second anticancer therapy is an HDAC inhibitor, such as ACY-1215 (Rocilinostat), or Tubastatin. In particular aspects, the second anticancer therapy comprises an immunotherapy, such as an immune checkpoint inhibitor. In specific aspects, the at least one immune checkpoint inhibitor is an anti-CTLA-4 antibody, an anti-PD-L1 antibody, and/or, an anti-PD-1 antibody. In some aspects, the immune checkpoint inhibitor is a human programmed cell death 1 (PD-1) binding antagonist, a PDL1 binding antagonist or a PDL2 binding antagonist. In certain aspects, the PD-1 binding antagonist is a monoclonal antibody or antigen binding fragment thereof. In some aspects, the PD-1 binding antagonist is nivolumab, pembrolizumab, CT-011, BMS 936559, MPDL328OA or AMP-224.

Yet still a further embodiment of the present disclosure provides a method for detecting a cancer in a subject comprising testing for the presence of elevated FGL2 relative to a control in a sample from the subject, wherein the testing comprises contacting the sample with an antibody of any of the embodiments and aspects described herein. In some aspects, the method is further defined as an in vitro method.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) FGL2 expression in normal brain and GBM tissue shown by immunohistochemistry. Increased staining is observed in the glioma tissues. (FIG. 1B) Flow cytometry analysis for the expression of F4/80 and CD206 in glioblastoma tumor cells treated with IgG control or F48 anti-FGL2 antibody. (FIG. 1C) Percentage of M2 macrophages in the glioblastoma tumors treated with IgG control or F48 anti-FGL2 antibody.

Figure 2:
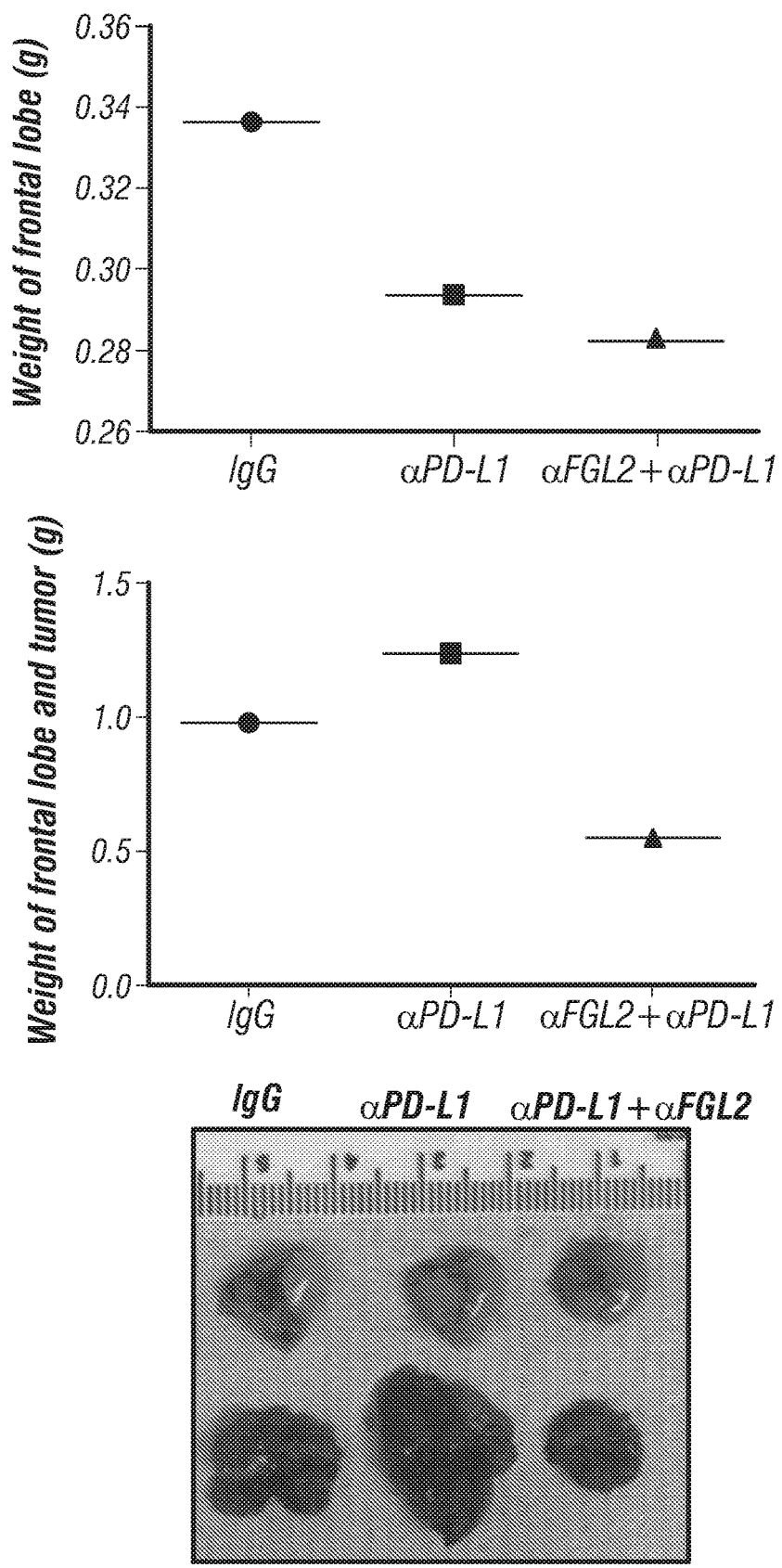

FIG. 2: Weight of frontal lobe and tumors are shown for mice inoculated with CT2A tumor cells and treated with IgG, anti-PDL1, or anti-PDL1+anti-FGL2 antibodies.

Figure 3A:
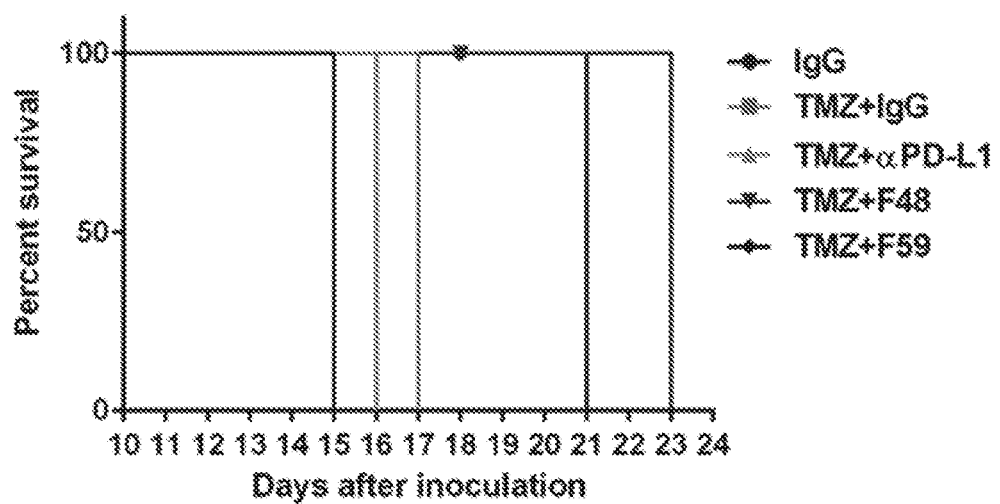
Figure 3B:
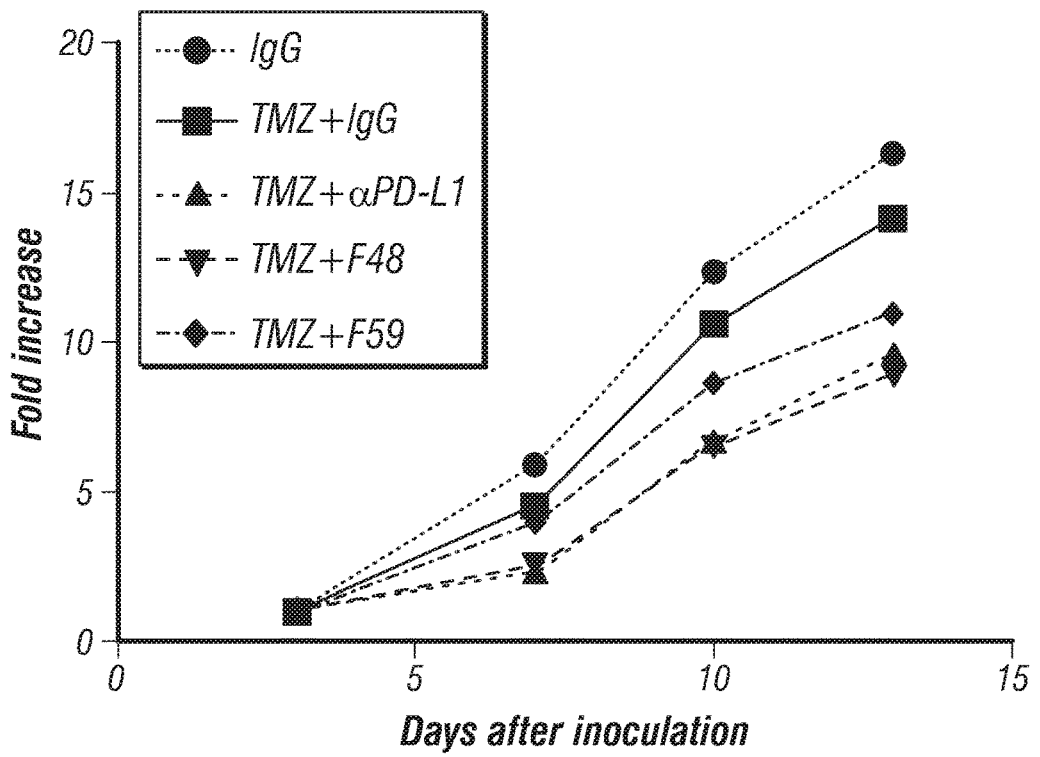
Figure 3B:
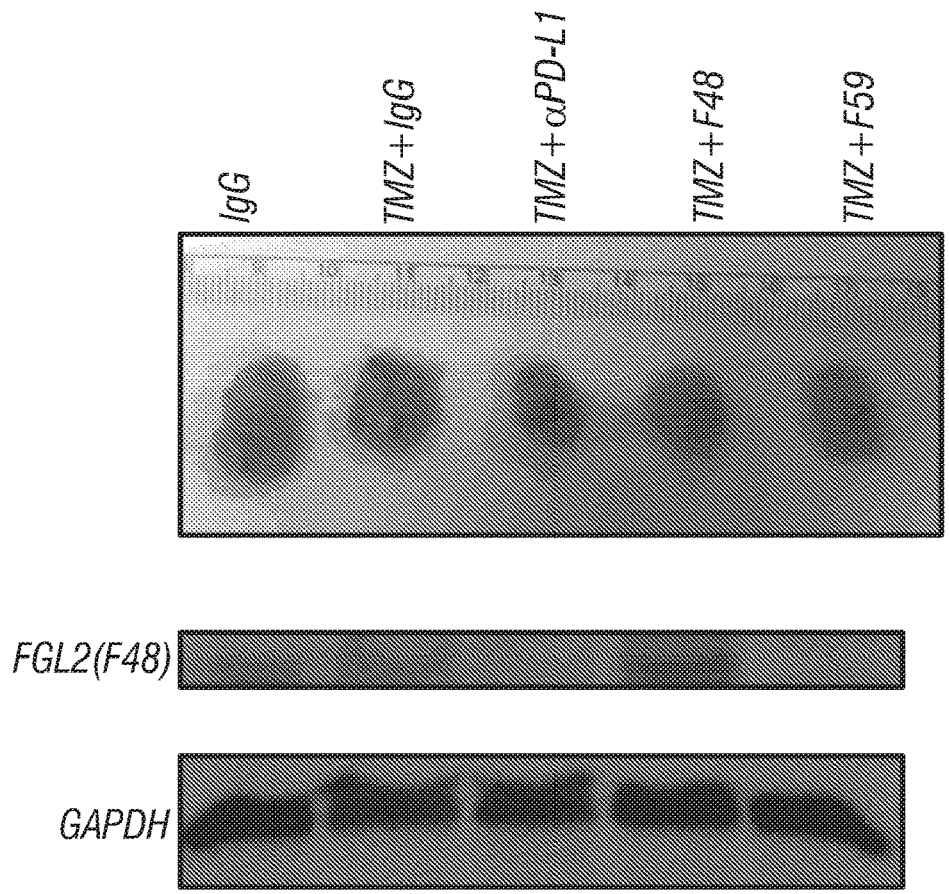
Figure 3C:
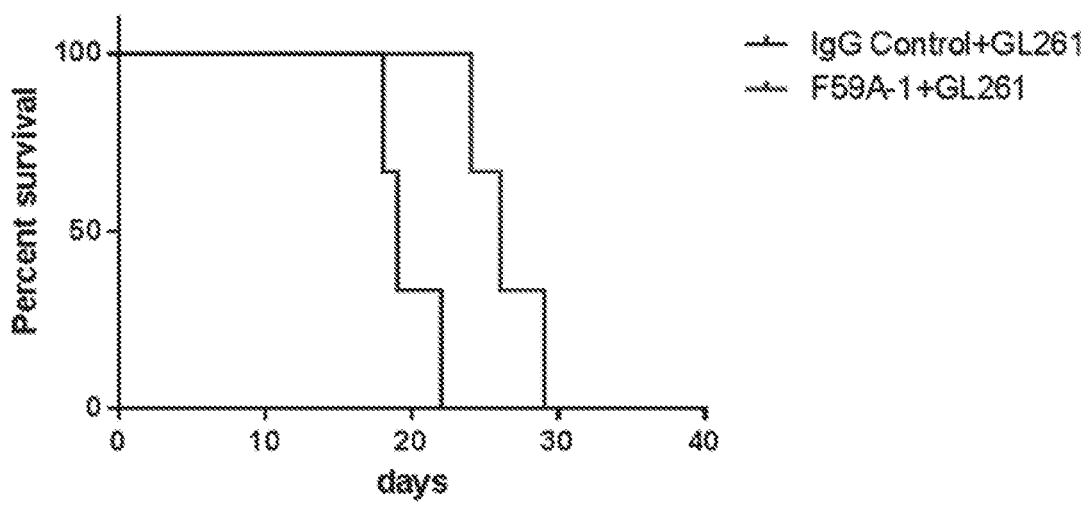

FIGS. 3A-3C: (FIG. 3A) Percent survival of glioma GL261 tumors treated with temozolomide (TMZ) in combination with IgG, F59, anti-PDL1, or F48. The lowest percent survival was observed in mice treated with IgG alone, followed by TMZ+anti-PDL1 antibody, and TMZ+ IgG. The highest percent survival was observed in mice treated with TMZ+F59 antibody followed by mice treated with TMZ+F48 antibody. (FIG. 3B) TMZ in combination with F48 or F59 antibody reduced tumor volume. Western blot analysis of FLG2 expression with various antibodies. FGLS expression is reduced in tumors treated with anti-FGL2 antibodies. (FIG. 3C) Percent survival of mice inoculated with GL261 and treated with IgG control or F59. F59 treatment resulted in increased percent survival.

Figure 4A:
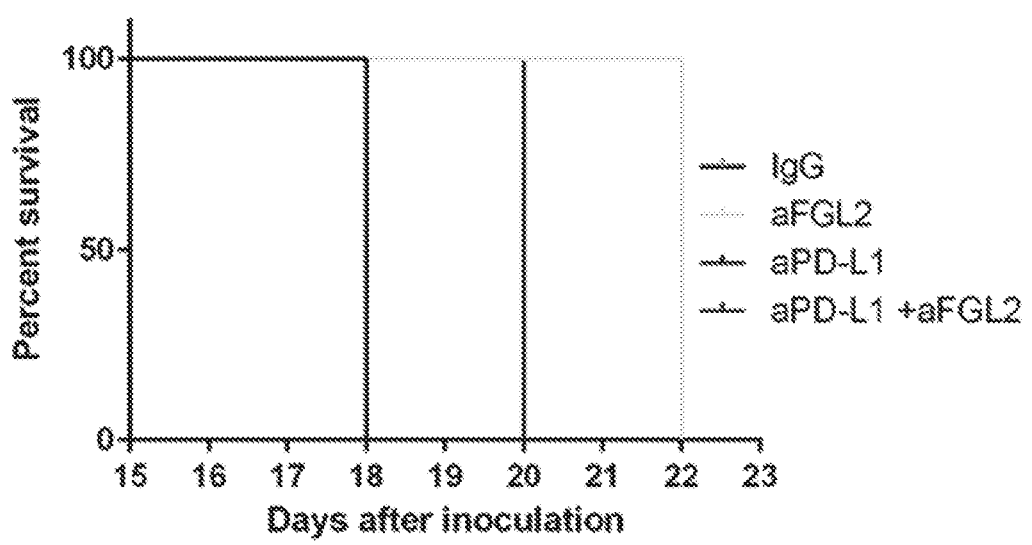
Figure 4B:
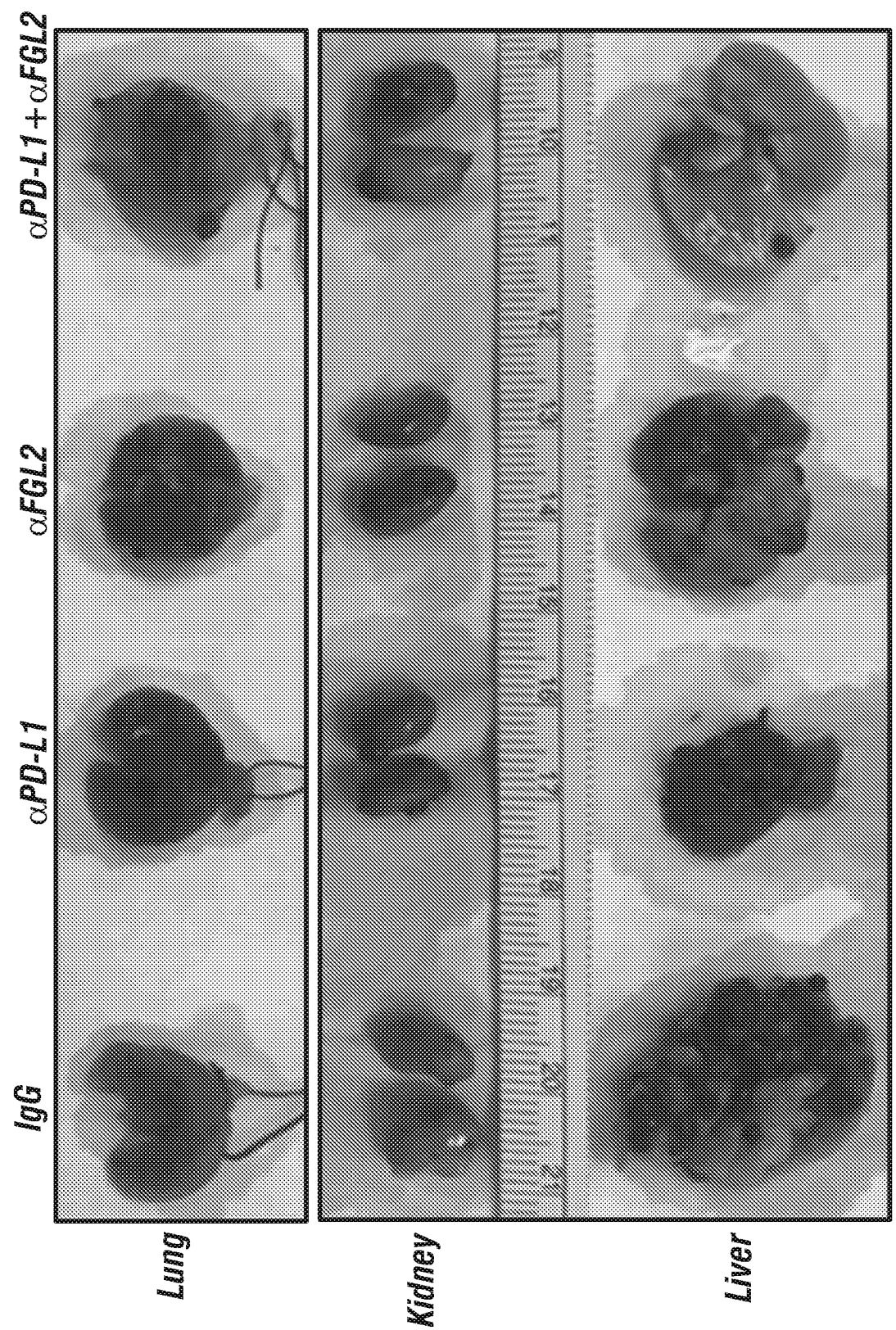

FIGS. 4A-4B: (FIG. 4A) Percent survival of Lewis lung carcinoma (LLC) tumor model mice treated with anti-FGL2 antibody F59 alone or in combination with anti-PDL1 antibody. The anti-PDL1 antibody and the anti-FGL2 antibody suppressed LLC progression. (FIG. 4B) Images of lungs, kidney, and livers of treated mice. F59 and PDL1 reduced the number of tumor nodules in both lungs and liver.

Figure 5A:
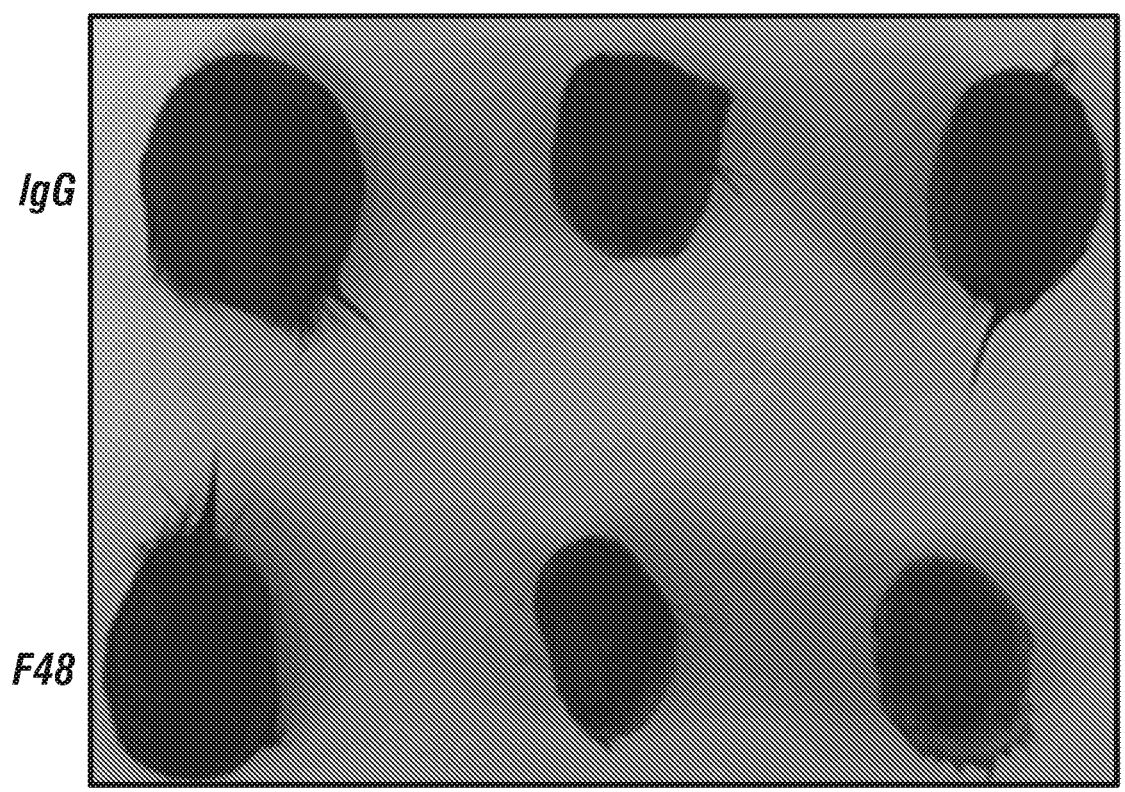
Figure 5A:
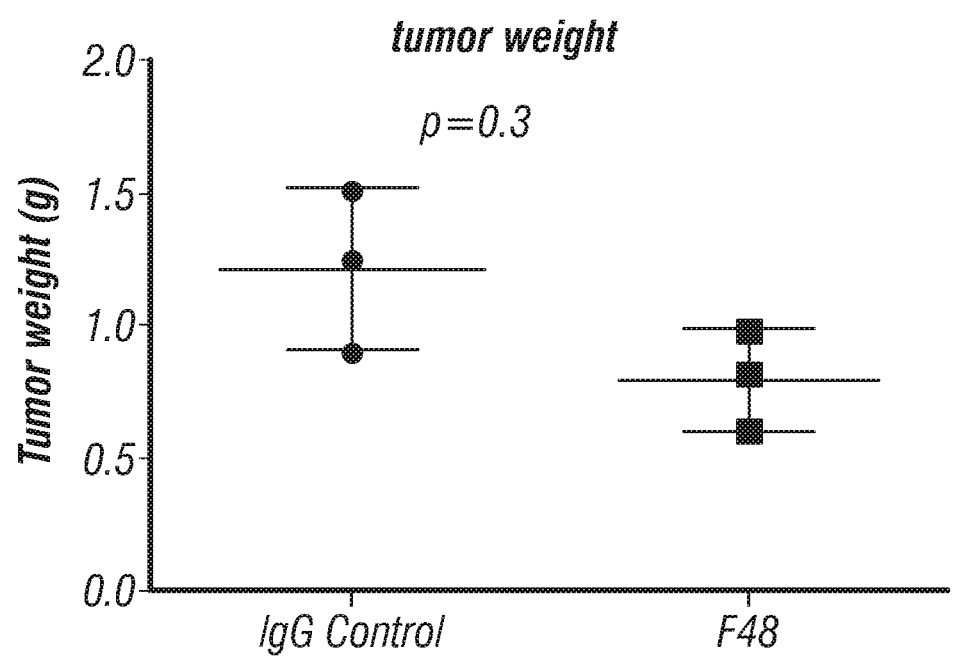
Figure 5B:
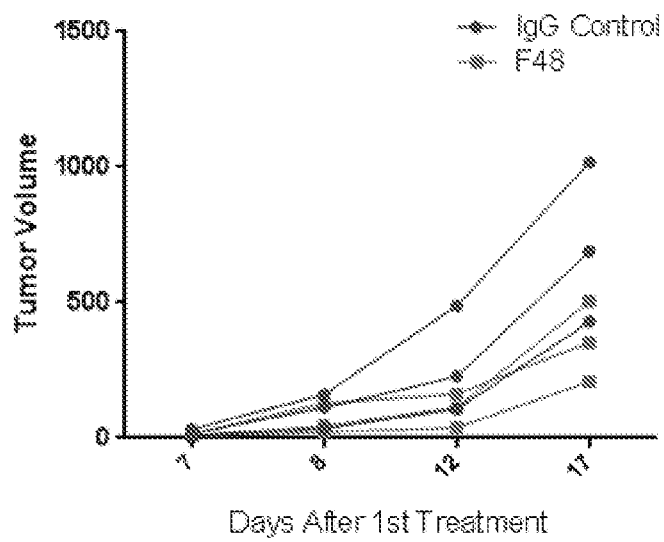
Figure 5C:
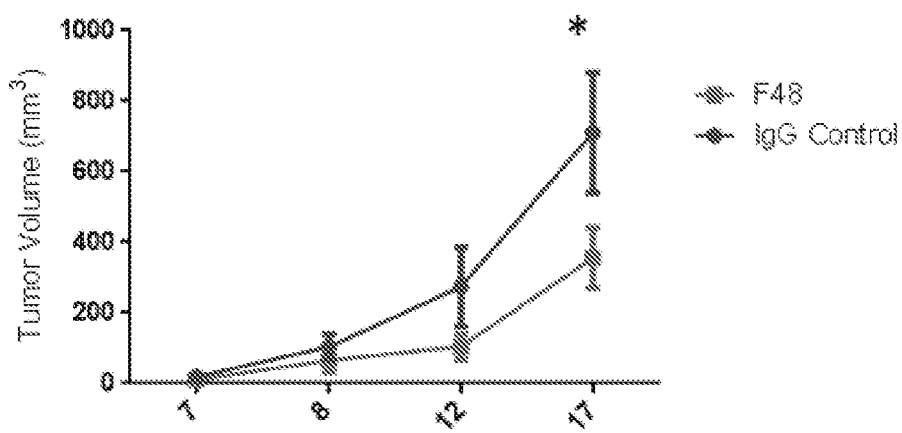

FIGS. 5A-5C: (FIG. 5A) Tumor weight of melanoma model mice treated with IgG control or F48 anti-FGL2 antibody along with images of tumors. (FIG. 5B) Tumor volume in individual mice treated with IgG control or F48 anti-FGL2 antibody up to 17 days after first treatment. (FIG. 5C) Tumor volume of mouse treated with IgG control or F48 anti-FGL2 antibody up to 17 days after first treatment.

Figure 6A:
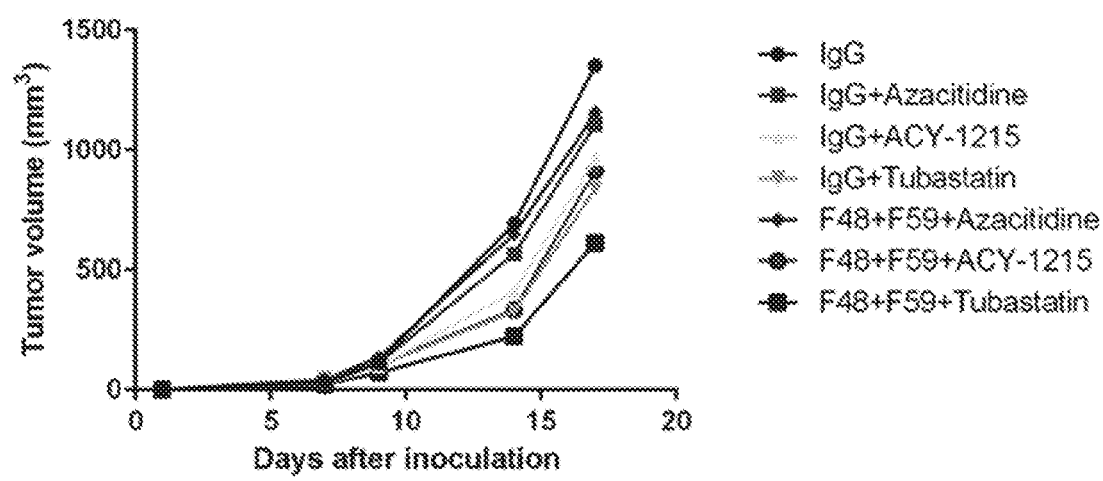
Figure 6B:
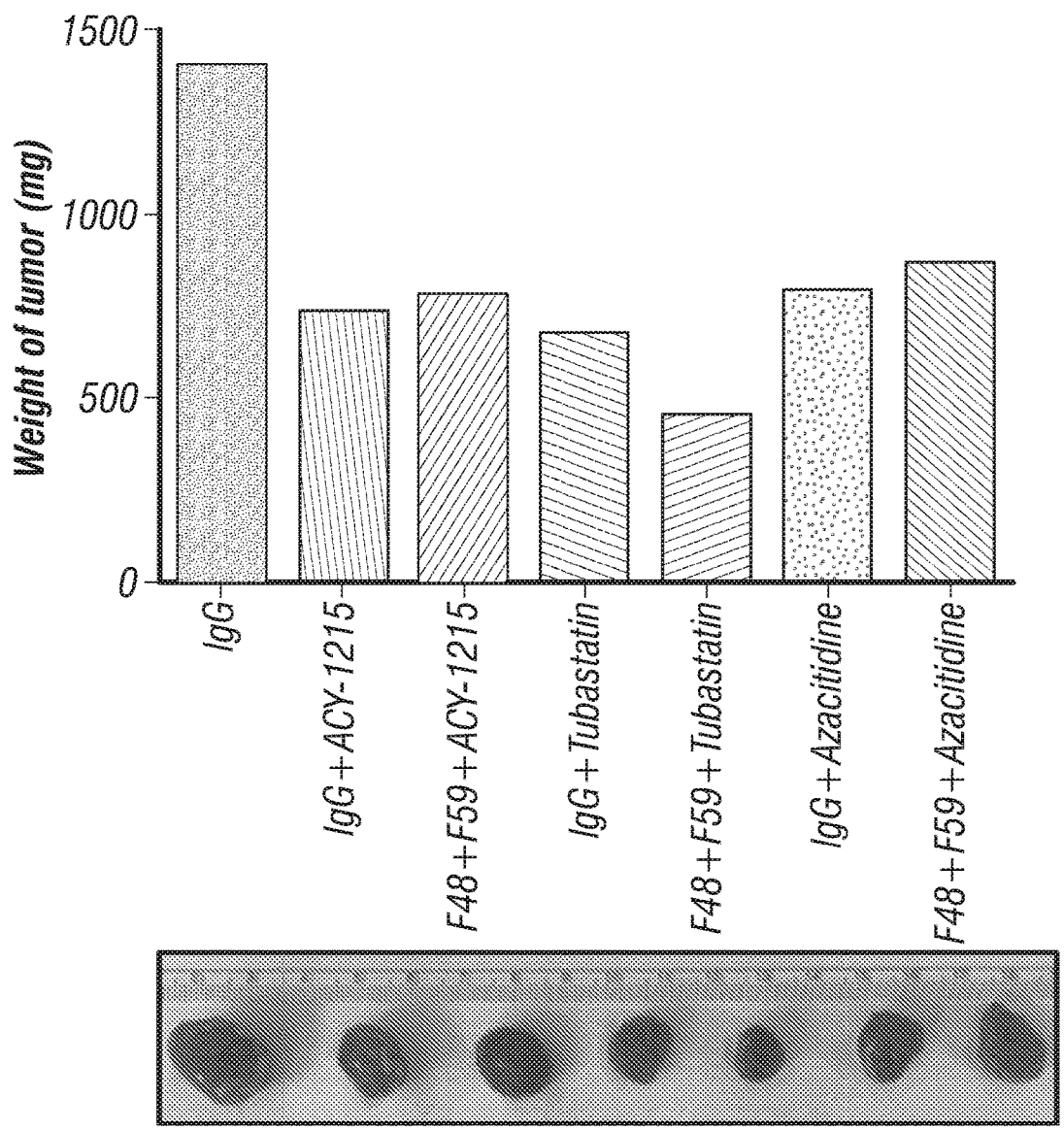
Figure 7A:
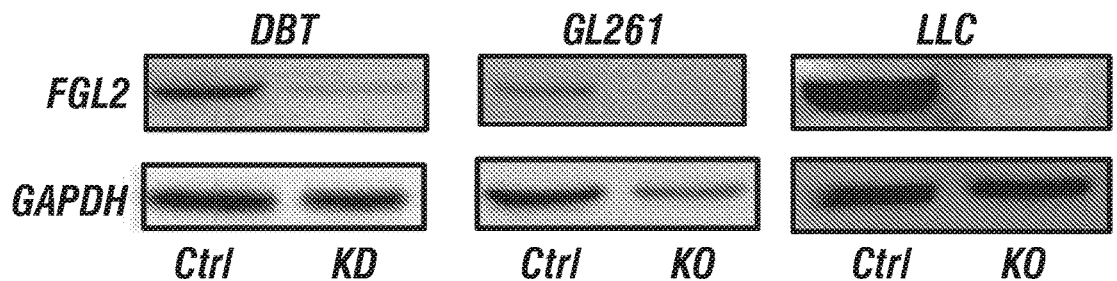
Figure 7B:
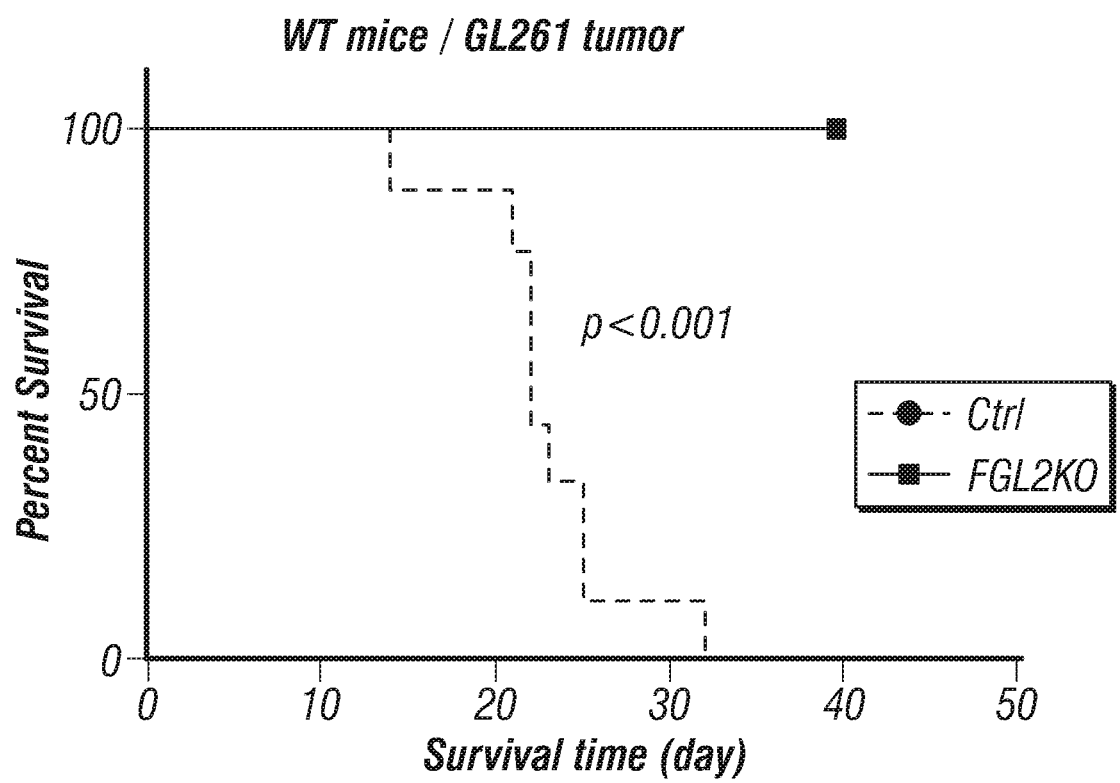
Figure 7C:
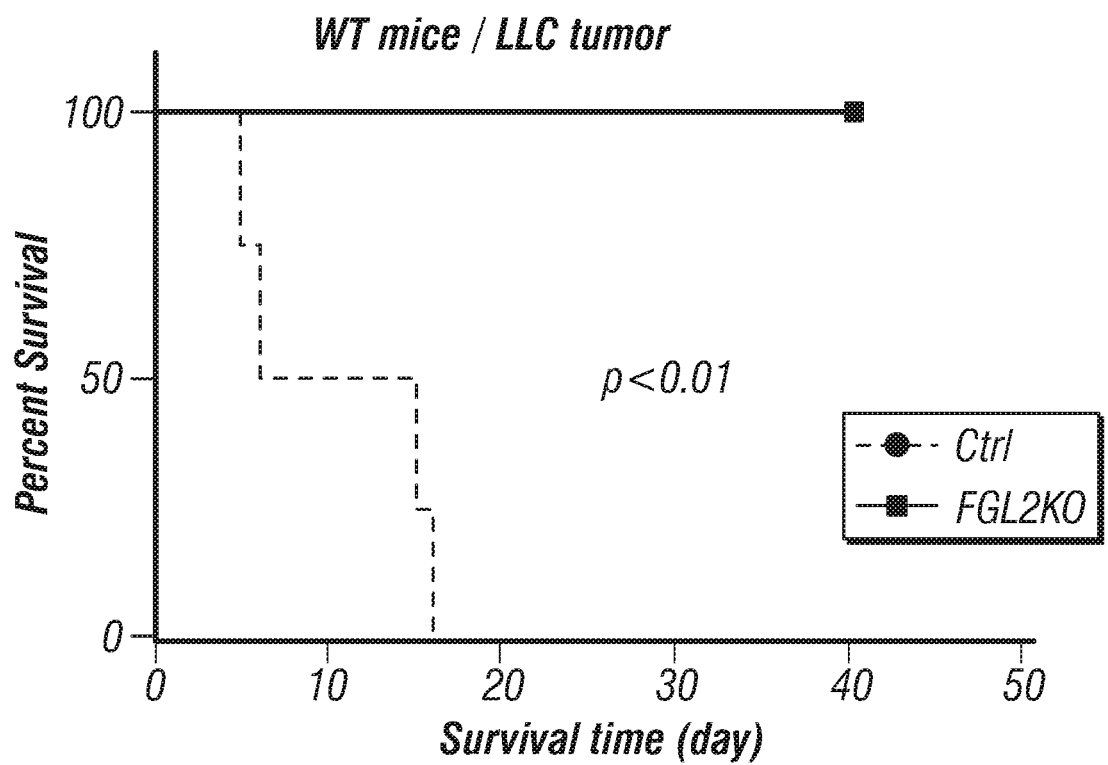
Figure 7D:
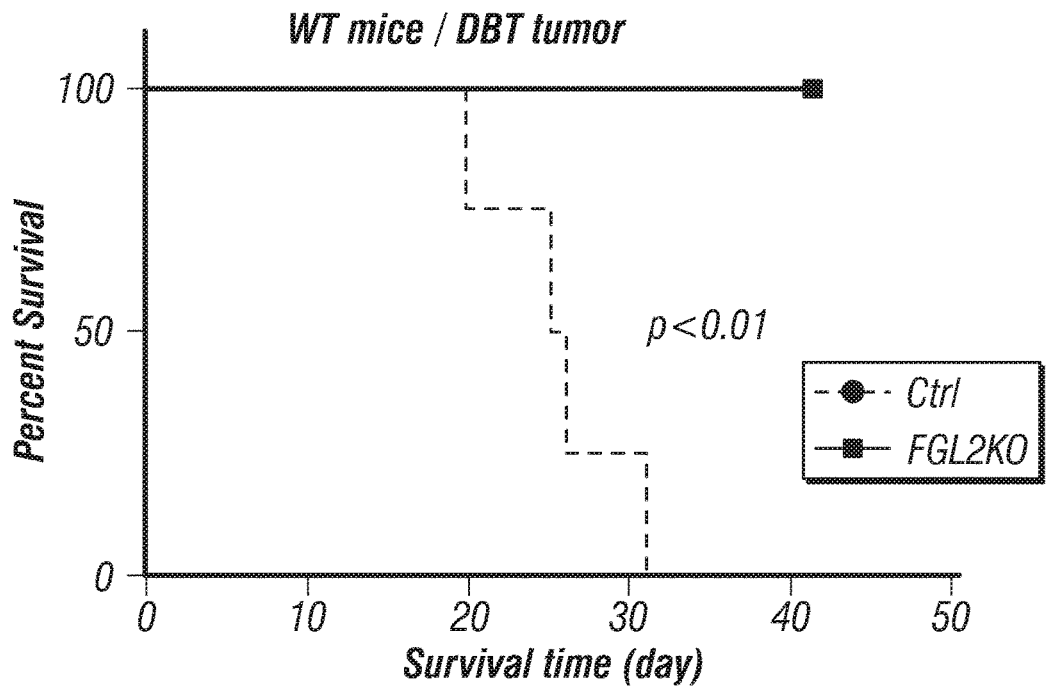
Figure 7E:
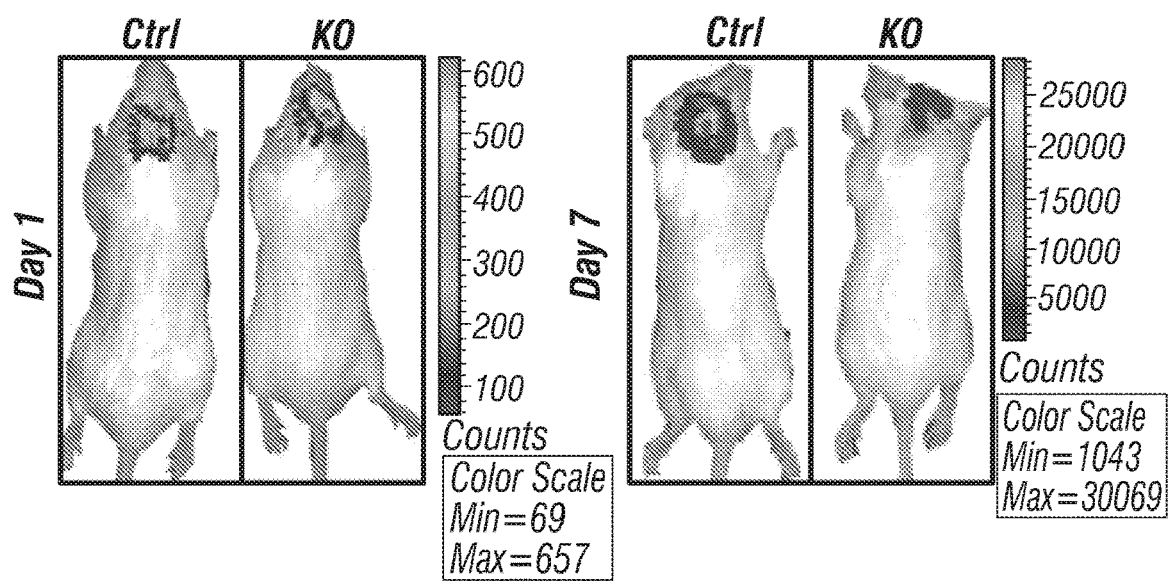

FIGS. 6A-6B: Tumor volume (FIG. 6A) and weight (FIG. 6B) of mice inoculated with B16F10 melanoma cells and treated with indicated therapies combinations.

FIGS. 7A-7E: CRISPR/Cas9-mediated FGL2 knockout in brain tumor cells abolishes tumor progression in murine models. (FIG. 7A) Expression level of FGL2 in three tumor cell lines, control (Ctrl) and FGL2-knockout (KO) or knockdown (KD) tumor cells was detected by western blotting. The western blots shown represent three independent experiments. (FIG. 7B) Survival curve of wild-type (WT) immunocompetent C57BL/6 mice implanted with GL261-Ctrl or GL261-FGL2KO tumor cells ($5 \times 10^4$ cells per mouse; n=9/group). Mice implanted with FGL2KO cells has higher percent survival. (FIG. 7C) Survival curve of WT immunocompetent C57BL/6 mice implanted with Lewis lung cancer (LLC)-Ctrl or LLC-FGL2KO tumor cells ($5 \times 10^4$ cells per mouse; n=4/group). Mice implanted with FGL2KO cells has higher percent survival. (FIG. 7D) Survival curve of WT immunocompetent BALB/C mice implanted with mouse astrocytoma (DBT)-Ctrl cells or DBT-FGL2KD tumor cells ($5 \times 10^4$ cells per mouse; n=4/group). Mice implanted with FGL2KO cells has higher percent survival. (FIG. 7E) Bioluminescence imaging showing DBT-Ctrl and DBT-FGL2KD tumors at day 1 and day 7 after tumor cell implantation.

Figure 8:
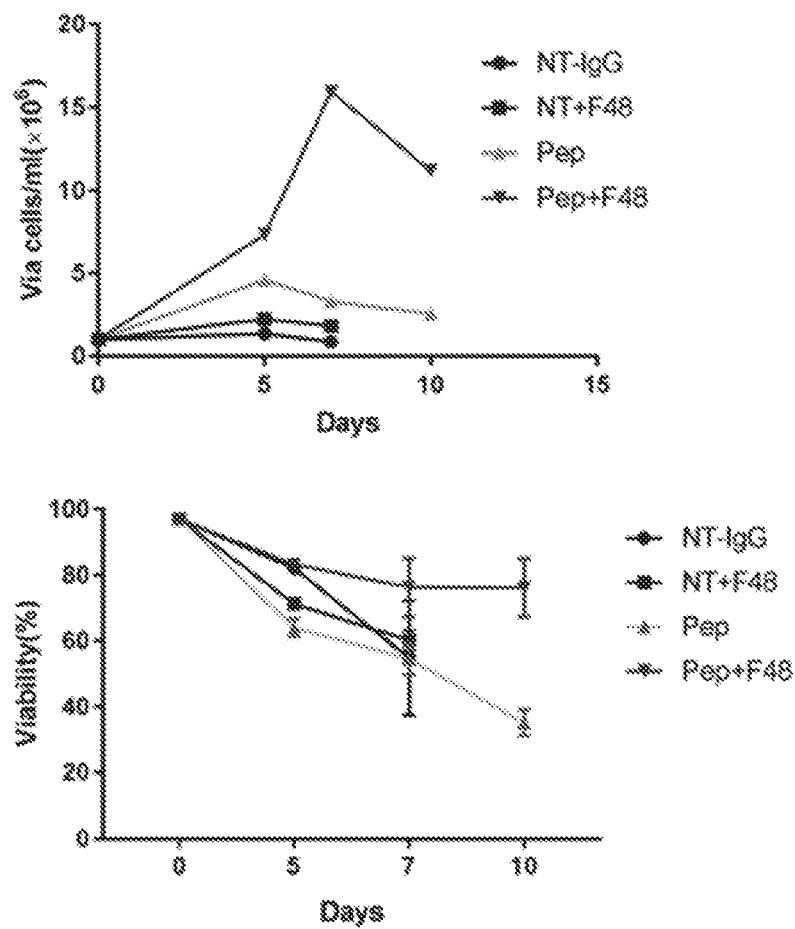

FIG. 8: FGL2 antibody promote activation-induced T cell growth. OT-I T cells were activated with αCD3/CD28 and then divided into different dishes to check the proliferation in the absence or presence of +OVA peptide (pep), absence or presence FGL2 mAb F48, and co-absence or presence of F48. Cell numbers were counted on different days.

DESCRIPTION OF ILLUSTRATIVE EMBODIMENTS

As discussed above, additional immunotherapies are needed for the treatment of cancers with redundant immunosuppressive mechanisms, such as glioblastoma. Accordingly, in certain embodiments, the present disclosure provides monoclonal antibodies to block FGL2.

In particular embodiments, the anti-FGL2 monoclonal antibodies provided herein are the F48 and F59 antibodies. Both F48 and F59 can block CD39 and CD73 regulatory T cell expression and share the property of cross-species binding. Given that the combination of CD39 and CD73 degrade ATP, ADP, and AMP to adenosine, they can be viewed as "immunological switches" that shift ATP-driven pro-inflammatory immune cell activity toward an anti-inflammatory state mediated by adenosine. CD39 and CD73 both play a role in regulating the function of several immune cell types, including lymphocytes, neutrophils, monocytes/macrophages, dendritic cells, and endothelial cells (Antonioli et al., 2013).

Thus, while current anti-immune checkpoint antibodies, such as PDL1 antibody, block one immune suppressive protein, the anti-FGL2 antibodies provided herein block a broad range of immune suppressive systems and immune checkpoints as FGL2 regulates the expression of multiple immune checkpoint proteins. Therefore, FGL2-blocking antibodies may prove to be more effective at treating cancers, including highly malignant and metastatic tumors which are known to express a high level of FGL2.

In the present studies, the anti-FGL2 antibodies were shown to be effective at treating multiple cancers, including glioblastoma, lung cancer, and melanoma, alone or in combination with other anti-cancer therapies. The anti-cancer therapies may include immune checkpoint inhibitors, such as an anti-PDL1 antibody, and/or chemotherapy, such as TMZ.

Accordingly, the present disclosure further provides methods for reversing immunosuppression by administering one or more of the anti-FGL2 antibodies provided herein. The methods may apply to the treatment of cancer or infectious diseases. In particular aspects, the anti-FGL2 may be used to suppress tumor growth and/or metastasis of tumors.

I. DEFINITIONS

"Treatment" and "treating" refer to administration or application of a therapeutic agent to a subject or performance of a procedure or modality on a subject for the purpose of obtaining a therapeutic benefit of a disease or health-related condition. For example, a treatment may include administration of an antibody that inhibits the FGL2 signaling.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAGS, BTLA, B7H3, B7H4, TIM3, and KIR are recognized in the art to constitute immune checkpoint pathways similar to the CTLA-4 and PD-1 dependent pathways (see e.g. Pardoll, 2012; Mellman et al., 2011).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

II. ANTI-FGL2 ANTIBODIES

In certain embodiments, an antibody or a fragment thereof that binds to at least a portion of FGL2 protein and inhibits FGL2 signaling are contemplated. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-FGL2 antibody is a monoclonal antibody or a humanized antibody.

Thus, by known means and as described herein, polyclonal or monoclonal antibodies, antibody fragments, and binding domains and CDRs (including engineered forms of any of the foregoing) may be created that are specific to FGL2 protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (U.S. Patent Publication No. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

In some embodiments, the anti-FGL2 antibody comprises CDRs 1-3 of the heavy chain of SEQ ID NO:2 (SYWMQ; EIDPSDSYTNYNQKFKG; NGNYYGSTYDY (SEQ ID NOs:5-7)) and the CDRs 1-3 of the light chain of SEQ ID NO:4 (RASQDVSNYLN; YTSRLHS; QQGNTLPPWT (SEQ ID NOs:8-10)). The anti-FGL2 antibody may have at least 80%, such as 85%, 90%, 91%, 92%, 93%, 94%, 95%, 96%, 97%, 98%, 99%, or 100%, sequence identity to SEQ ID NOs:1-4. The heavy and light chain sequences are depicted below with the CDRs underlined and the leader sequence in italics.

F48 Heavy Chain
(SEQ ID NO: 1)
*ATGGGATGGAGCTGTATCATCCTCTTCTTGGTAGCAACAGCTACAGGTGT*

*CCACTCTCAGGTCCAACTGCAGCAGCCTGGGGCTGAGCTTGTGAAGCCTG*

*GGGCTTCAGTGAAGCTGTCCTGCAAGGCTTCTGGCTACACCTTCGCC*AGC

TACTGGATGCAGTGGGTAAAACAGAGGCCTGGACAGGGCCTTGAGTGGAT

CGGAGAGATTGATCCTTCTGATAGCTATACTAACTACAATCAAAAGTTCA

AGGGCAAGGCCACATTGACTGTAGACACATCCTCCAACACAGCCTACATG

CAGCTCAGCAGCCTGACATCTGAGGACTCTGCGGTCTATTACTGTGCAAG

AAATGGGAATTACTACGGTAGTACCTACGACTACTGGGGCCAAGGCACCA

CTCTCACAGTCTCCTCA

F48 Heavy Chain
(SEQ ID NO: 2)
*MGWSCIILFLVATATGVHS*QVQLQQPGAELVKPGASVKLSCKASGYTFA<u>S</u>

<u>YWMQ</u>WVKQRPGQGLEWIG<u>EIDPSDSYTNYNQKFKG</u>KATLTVDTSSNTAYM

QLSSLTSEDSAVYYCAR<u>NGNYYGSTYDY</u>WGQGTTLTVSS

F48 Light Chain
(SEQ ID NO: 3)
*ATGATGTCCTCTGCTCAGTTCCTTGGTCTCCTGTTGCTCTGTTTTCAAGG*

*TACCAGATGT*GATATCCAGATGACACAGACTACATCCTCCCTGTCTGCCT

CTCTGGGAGACAGAGTCACCATCAGTTGC<u>AGGGCAAGTCAGGACGTTAGC</u>

<u>AATTATTTAAAC</u>TGGTATCAGCAGAAACCAGATGGATCTGTTAAACTCCT

GATC<u>TACTACACTTCAAGATTACACT</u>CAGGAGTCCCATCAAGGTTCAGTG

GCAGTGGGTCTGGAGCACATTATTCTCTCACCATTAGCAACCTGGAGCAA

GAAGATATTGCCACTTACTTTTGC<u>CAACAGGGTAATACGCTTCCTCCGTG</u>

<u>GACG</u>TTCGGTGGAGGCACCAAGCTGGAAATCAAG

F48 Light Chain
(SEQ ID NO: 4)
*MMSSAQFLGLLLLCFQGTRC*DIQMTQTTSSLSASLGDRVTISC<u>RASQDVS</u>

<u>NYLN</u>WYQQKPDGSVKLLIY<u>YTSRLHS</u>GVPSRFSGSGSGAHYSLTISNLEQ

EDIATYFC<u>QQGNTLPPWT</u>FGGGTKLEIK

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a FGL2 extracellular domain (ECD) protein, in order to produce antibodies specific for FGL2 protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a FGL2 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells ($CD45^+CD5^-CD19^+$) may be isolated from freshly prepared rabbit peripheral blood mononuclear cells of immunized rabbits and further selected for FGL2 binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. FGL2 specific binding Fab may be selected out through multiple rounds enrichment panning and sequenced. Selected FGL2 binding hits may be expressed as full-length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881, 557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939, 350; 3,996,345; 4,196,265; 4,275,149; 4,277,437; 4,366, 241; 4,469,797; 4,472,509; 4,606,855; 4,703,003; 4,742, 159; 4,767,720; 4,816,567; 4,867,973; 4,938,948; 4,946, 778; 5,021,236; 5,164,296; 5,196,066; 5,223,409; 5,403, 484; 5,420,253; 5,565,332; 5,571,698; 5,627,052; 5,656, 434; 5,770,376; 5,789,208; 5,821,337; 5,844,091; 5,858, 657; 5,861,155; 5,871,907; 5,969,108; 6,054,297; 6,165, 464; 6,365,157; 6,406,867; 6,709,659; 6,709,873; 6,753, 407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946, 546, which is incorporated herein by reference. These techniques are further described in: Marks (1992); Stemmer (1994); Gram et al. (1992); Barbas et al. (1994); and Schier et al. (1996).

It is fully expected that antibodies to FGL2 will have the ability to neutralize or counteract the effects of FGL2 regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds FGL2.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against FGL2, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radio-labels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

III. METHODS OF USE

Certain aspects of the present embodiments can be used to prevent or treat a disease or disorder associated with FGL2 signaling. Signaling of FGL2 may be reduced by any suitable drugs to prevent cancer cell proliferation. Preferably, such substances would be an anti-FGL2 antibody to reverse mechanisms which suppress the immune system.

In certain embodiments, the compositions and methods of the present embodiments involve an antibody or an antibody fragment against FGL2 to inhibit its activity in cancer cell proliferation, in combination with a second or additional therapy. Such therapy can be applied in the treatment of any disease that is associated with FGL2-mediated cell proliferation. For example, the disease may be cancer.

Accordingly, in some embodiments, provided herein are methods for treating or delaying progression of cancer in an individual comprising administering to the individual an effective amount an anti-FGL2 antibody. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Combination Treatments

In some embodiments, the methods of the present disclosure comprise the combination of an anti-FGL2 antibody and an additional anti-cancer therapeutic.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

| | | | | | | |
|---|---|---|---|---|---|---|
| A/B/A | B/A/B | B/B/A | A/A/B | A/B/B | B/A/A | A/B/B/B B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or $V_H$ and/or $V_L$ domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the $V_H$ region of ipilimumab, and the CDR1, CDR2 and CDR3 domains of the $V_L$ region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Characterization of Anti-FGL2 Antibodies

Figure 1A:
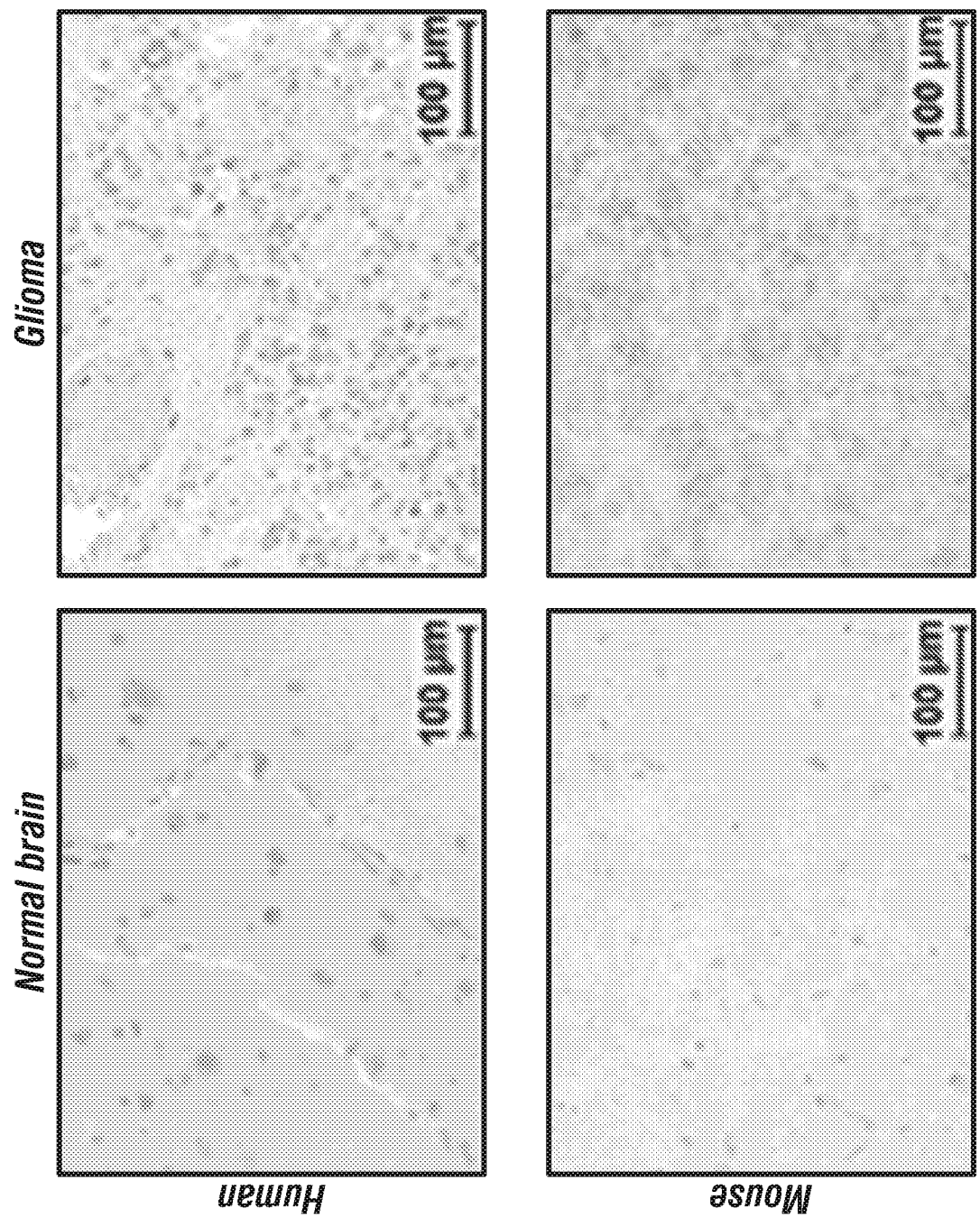
FIGS. 1A-1C.

The present studies developed and characterized two anti-FGL2 monoclonal antibodies, F48 and F59. Both of the antibodies were able to block CD39 and CD73 regulatory T cell expression. The effects of the anti-FGL2 antibodies were evaluated alone and in combination with other anti-cancer therapies such as anti-PDL1 antibody and chemotherapy on several mouse tumor models, including glioblastoma, melanoma, and lung cancer. In particular, immunohistochemistry of normal brain tissue and glioblastoma tissue shows that FGL2 has increased expression in glioblastoma (FIG. 1A).

Figure 1B:
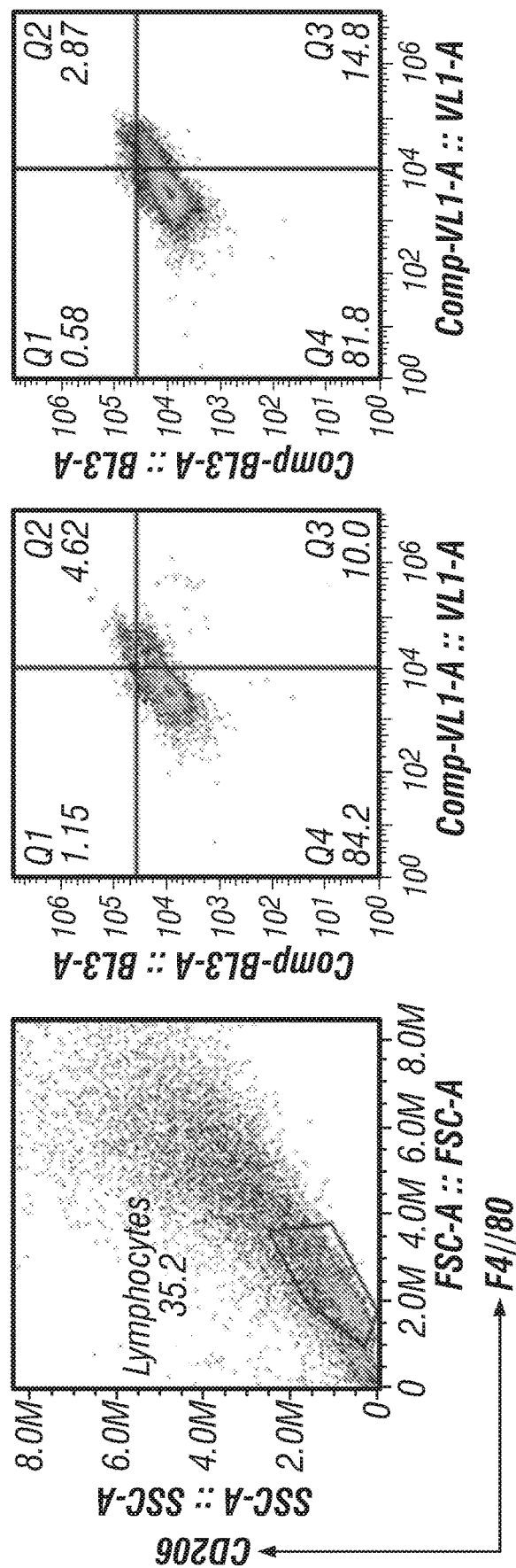
Figure 1C:
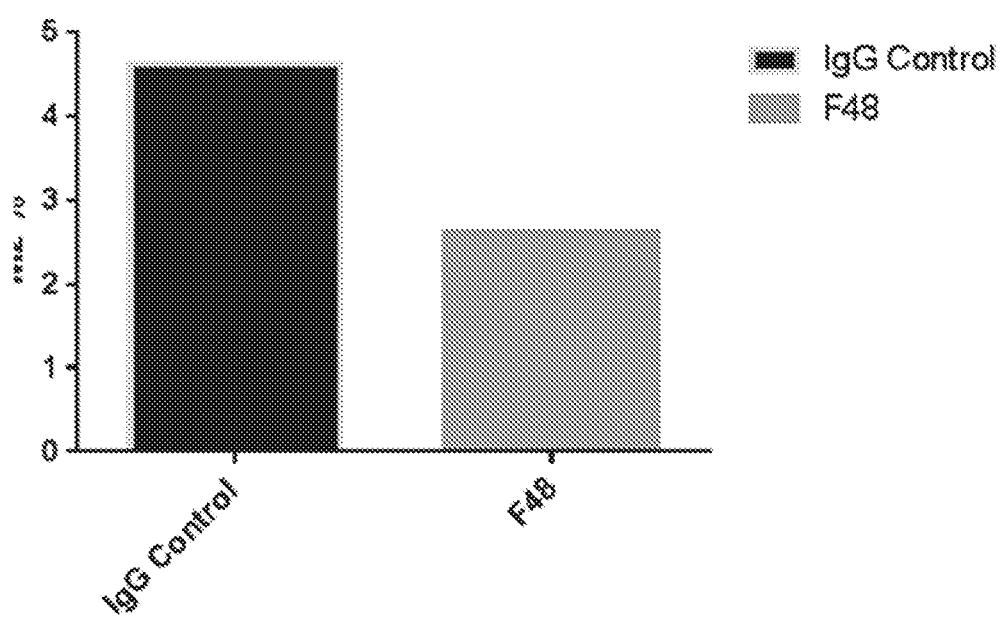

To screen for the anti-FGL2 antibody F48 function in mice, GL261 glioblastoma cells ($1 \times 10^5$ in 30 µL) were injected into the back of mice by subcutaneous injection. The first treatment with antibody comprised 100 µg antibody by intravenous injection starting at about 5-7 days after tumor inoculation. The antibody treatment was repeated every 3 days and the mice were sacrificed at about 14-21 days. It was observed that the F48 antibody treatment caused a suppression of the percentage of M2 cell population in the tumors (FIG. 1B).

A study was designed to evaluate the effect of PD-L1 antibody and FGL2 antibody on glioblastoma growth (Table 1). Mice were inoculated with CT2A tumor cells and treated with control IgG, anti-PDL1 antibody, or F59-1+anti-PDL1 antibody at a concentration of 200 µg per mouse. The mice were sacrificed at day 21. The combination of the anti-PDL1 antibody and the FGL2 antibody was found to inhibit CT2A growth (FIG. 2).

TABLE 1

Treatment groups for glioblastoma tumor model.

| Groups | Mouse strain | Tumor cells | Treatment | Dosage (ug/mouse) | Mouse number | Sacrifice date |
|---|---|---|---|---|---|---|
| 1 | GFP | CT2A | IgG | 200 | 1 | 21 day |
| 2 | GFP | CT2A | Anti-PD-L1 | 200 | 1 | 21 day |
| 3 | GFP | CT2A | F59-1 + Anti-PD-L1 | 200 + 200 | 1 | 21 day |

Next, the effect of the combination of temozolomide (TMZ) and anti-PDL1+anti-FGL2 antibody was determined on the mouse glioma GL261 tumor model progression in vivo.

TABLE 2

Combination treatment groups for glioblastoma.

| Group | GL261 |
|---|---|
| A. | saline |
| B. | 20 mg/kg TMZ + 200 μg IgG |
| C. | 20 mg/kg TMZ + 200 μg F59 |
| D. | 20 mg/kg TMZ + 200 μg αPD-L1 |
| E. | 20 mg/kg TMZ + 200 μg F48 |

Percent survival of glioma GL261 tumors treated with temozolomide (TMZ) in combination with IgG, F59, anti-PDL1, or F48 (FIG. 3). The lowest percent survival was observed in mice treated with IgG alone, followed by TMZ+anti-PDL1 antibody, and TMZ+IgG. The highest percent survival was observed in mice treated with TMZ+F59 antibody followed by mice treated with TMZ+F48 antibody. Thus, both F48 and F59 significantly improve glioma survival.

The effect of anti-FGL2 antibody was also evaluated in a Lewis lung carcinoma (LLC) murine model (Table 3). It was observed that the combination of F59 antibody and anti-PDL1 antibody slightly suppressed LLC progression as seen by an increase in percent survival (FIG. 4A). The combination of the two antibodies was observed to reduce the number of tumor nodules in both the lungs and liver (FIG. 4B).

TABLE 3

Treatment groups for lung cancer tumor model.

| Groups | Mouse strain | Tumor cells | Treatment | Dosage (ug/mouse) | Mouse number | Survival |
|---|---|---|---|---|---|---|
| 1 | C57 | LLC | Anti-PD-L1 | 200 | 1 | 20 days after inoculation |
| 2 | C57 | LLC | F59-1 + Anti-PD-L1 | 200 + 200 | 1 | 22 days after inoculation |
| 3 | C57 | LLC | F59-1 | 200 | 1 | 22 days after inoculation |
| 4 | C57 | LLC | IgG | 200 | 1 | 18 days after inoculation |

In addition, the effect of the FGL2 antibodies were tested on the melanoma B16F10 tumor model (Table 4). The combination of both F48 and F59 anti-FGL2 antibodies in combination with Tubastatin resulted in the greatest decrease in tumor volume (FIGS. 6A-6B).

TABLE 4

Treatment groups for melanoma model.

| Group | Treatment | N |
|---|---|---|
| A | IgG | 1 |
| B | IgG + ACY-1215(50 mg/kg i.p.) | 1 |
| C | IgG + Tubastatin(75 mg/kg i.p.) | 1 |
| D | IgG + Azacitidine(0.7 mg/kg i.v.) | 1 |
| E | F48(100ug) + F59(100ug) + ACY-1215(50 mg/kg i.p.) | 1 |
| F | F48(100ug) + F59(100ug) + Tubastatin(75 mg/kg i.p.) | 1 |
| G | F48(100ug) + F59(100ug) + Azacitidine(0.7 mg/kg i.v.) | 1 |

In addition, it was shown that CRISPR/Cas9-mediated FGL2 knockout in brain tumor cells abolishes tumor progression in murine models (FIG. 7). Mice implanted with FGL2KO tumor cells had higher percent survival than mice implanted WT tumor cells in all of the mouse models tested including LLC and astrocytoma.

Thus, the anti-FGL2 antibodies were shown to be effective at decreasing tumor growth and metastasis in several cancer models.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Antonioli et al., Trend Mol Med., 19(6):355-367, 2013.
Kabat et al., Sequences of Proteins of Immunological Interest, National Institutes of Health, Bethesda, Md., 1987.
Leal et al., 2014
Mellman et al., Nature 480:480-489, 2011.
Pardoll, Nature Rev Cancer 12:252-264, 2012.
Selzner et al., Rambam Maimonides Med J., 1(1):e0004, 2010.
U.S. Pat. No. 4,870,287
U.S. Pat. No. 5,091,513
U.S. Pat. No. 5,091,513
U.S. Pat. No. 5,760,395
U.S. Pat. No. 6,881,557
U.S. Patent Publication No. 20050214860
Yan et al., J Natl Cancer Inst, 107(8), 2015.

What is claimed is:

1. An isolated monoclonal antibody, wherein the antibody specifically binds FGL2 and comprises:
   (a) a first $V_H$ CDR is identical to SEQ ID NO: 5;
   (b) a second $V_H$ CDR is identical to SEQ ID NO: 6;
   (c) a third $V_H$ CDR is identical to SEQ ID NO: 7;
   (d) a first $V_L$ CDR is identical to SEQ ID NO: 8;
   (e) a second $V_L$ CDR is identical to SEQ ID NO: 9; and
   (f) a third $V_L$ CDR is identical to SEQ ID NO: 10.

2. The antibody of claim 1, wherein the antibody comprises a $V_H$ domain at least about 80% identical to the $V_H$ domain of F48 (SEQ ID NO:2) and a $V_L$ domain at least about 80% identical to the $V_L$ domain of F48 (SEQ ID NO:4).

3. The antibody of claim 2, wherein the antibody comprises a $V_H$ domain identical to the $V_H$ domain of F48 (SEQ ID NO:2) and a $V_L$ domain identical to the $V_L$ domain of F48 (SEQ ID NO:4).

4. The antibody of claim 1, wherein the antibody is recombinant.

5. The antibody of claim 1, wherein the antibody is an IgG, IgM, IgA or an antigen-binding fragment thereof.

6. The antibody of claim 1, wherein the antibody is a Fab', a F(ab')2, a F(ab')3, a monovalent scFv, or a bivalent scFv.

7. The antibody of claim 1, wherein the antibody is a human, humanized antibody or de-immunized antibody.

8. The antibody of claim 1, wherein the antibody is conjugated to an imaging agent, a chemotherapeutic agent, a toxin or a radionuclide.

9. A composition comprising an antibody of claim 1 in a pharmaceutically acceptable carrier.

10. An isolated polynucleotide molecule comprising a nucleic acid sequence encoding an antibody of claim 1.

11. An isolated host cell comprising one or more polynucleotide molecule(s) encoding an antibody of claim 1.

12. A method of manufacturing an antibody comprising:
   (a) expressing one or more polynucleotide molecule(s) encoding a $V_L$ and $V_H$ chain of an antibody of claim 1 in an isolated cell; and
   (b) purifying the antibody from the isolated cell.

13. A method for detecting a cancer in a subject comprising testing for the presence of elevated FGL2 relative to a control in a sample from the subject, wherein the testing comprises contacting the sample with an antibody of claim 1.

14. A method for treating a subject having a cancer comprising administering an effective amount of an antibody of claim 1 to the subject.

15. The method of claim 14, further comprising administering at least a second anticancer therapy to the subject.

16. The method of claim 15, wherein the second anticancer therapy is chemotherapy.

17. The method of claim 16, wherein the chemotherapy is temolozolomide or azacitidine.

18. The method of claim 15, wherein the second anticancer therapy is an histone deacetylase (HDAC) inhibitor.

19. The method of claim 18, wherein the HDAC inhibitor is ACY-1215 (rocilinostat), or Tubastatin.

20. The method of claim 14, wherein the subject is administered a PD-1 binding antagonist selected from the group consisting of nivolumab, pembrolizumab, CT-011, BMS 936559, MPDL328OA and AMP-224.

* * * * *